(12) United States Patent
Frias Peña

(10) Patent No.: US 7,402,324 B1
(45) Date of Patent: Jul. 22, 2008

(54) PROCESS FOR PREPARING AQUEOUS EXTRACTS OF PLANTS AND EXTRACTS SO OBTAINED

(75) Inventor: José Manuel Frias Peña, Barcelona (ES)

(73) Assignee: Bomsund Grupo Asesor, S.L. (ES)

( * ) Notice: Subject to any disclaimer, the term of this patent is extended or adjusted under 35 U.S.C. 154(b) by 414 days.

(21) Appl. No.: 10/432,696

(22) PCT Filed: Nov. 27, 2000

(86) PCT No.: PCT/IB00/01947

§ 371 (c)(1),
(2), (4) Date: Dec. 24, 2003

(87) PCT Pub. No.: WO02/41908

PCT Pub. Date: May 30, 2002

(51) Int. Cl.
*A61K 36/00* (2006.01)
*A61K 9/00* (2006.01)
(52) U.S. Cl. ........................... 424/725; 424/400
(58) Field of Classification Search .................. 424/725
See application file for complete search history.

(56) References Cited

U.S. PATENT DOCUMENTS 6,143,337 A * 11/2000 Fishman et al. ............. 426/241

FOREIGN PATENT DOCUMENTS

| EP | 0 934 746 | 8/1999 |
|---|---|---|
| FR | 2 733 419 | 10/1996 |

* cited by examiner

*Primary Examiner*—Christopher R. Tate
*Assistant Examiner*—Randall Winston
(74) *Attorney, Agent, or Firm*—Schiff Hardin LLP

(57) ABSTRACT

The present invention provides a method for preparing aqueous extracts of vegetals, particularly of plants, which comprises the steps of a) decontamination of the plant, b) comminuting the plant, c) treatment of the comminuted plant with a laser radiation, d) suspension of the mixture obtained in step c) in water, e) maceration of the suspension obtained in step d), and f) separation of the resulting liquid. The invention also provides the compositions obtained by the present method, some of which find application in medicine, particularly in the treatment of immune-suppressant diseases such as cancer, tuberculosis, influenza, common cold and AIDS, or in the treatment of viral diseases such as hepatitis.

22 Claims, No Drawings

PROCESS FOR PREPARING AQUEOUS EXTRACTS OF PLANTS AND EXTRACTS SO OBTAINED

BACKGROUND OF THE INVENTION

1. Field of the Invention

The present invention relates to a process for preparing aqueous extracts of plants and to the aqueous extracts thus obtained, some of which find application in medicine, particularly in the treatment of immune suppressant diseases or in the treatment of viral diseases.

2. Description of the Related Art

Plants and, in general, vegetals, remain an important source of active compositions and compounds employed in medicine. New plants, new compounds present in plants or even modifications of compounds present in plants are of potential interest to the phitochemical industry.

The methods employed in the extraction of the components of vegetals and plants are of great importance regarding not only the yields of the compounds to be obtained, but also the chemical nature of the compounds which can in fact be gained.

The usual methods employed in the phitochemical industry are based on the extraction of the comminuted plant or vegetal with water or steam, with organic solvents, or with mixtures of water and organic solvents such as water and alcohols. The inclusion of a maceration step is also well known in the art. Finally, the separation of the aqueous extract from the solid phase can be effected by conventional methods such as decantation, centrifugation or filtration. Additional chemical treatments to modify the structure of the compounds present in the plants can also be effected. See Dr. Pio Font Quer, "Medicinal Plants. The updated Discorides" Ed. Labor, S.A., 12$^{th}$ Edition, 1990.

The French patent FR 2733419 ("the '419 patent") describes the preparation of extracts of a mixture of at least three different plants selected from the genus *Geranium*, *Plantago* and *Calendula* by steeping 300-400 g of fresh *Geranium robertanium* leaves, 10-50 g of dried *Plantago lanceolata* leaves and 10-50 g dried *Calendula officinalis* leaves in 3 l. of water at 15-30° C. for 3-15 days. According to the '419 patent, the composition thus obtained can be used in the treatment of cancer. However, these extracts produce non-satisfactory activity, as reflected in the examples below.

The European patent application EP 0 934 746 A ("the '746 application") discloses the preparation of an aqueous extract of plants from the genus *Geranium* and *Plantago* as well as from the species *Calendula officinalis*, in which these extracts are obtained from the following amounts in grams of these plants in water: 10 to 60 of dried *Geranium sibiricun* or 300 to 360 of fresh *Geranium sibiricum*, 10 to 60 of dried *Plantago lanceolata*, and 10 to 60 of dried *Calendula Officinalis* in 300 grams of water. The method for producing these aqueous extracts comprises macerating the comminuted plants in water before press-filtering the mixture and submitting it to a centrifugal treatment. According to the '746 application, this extract may be used in oncological practice as part of a cancer therapeutic program. However, these extracts produce non-satisfactory activity as reflected in the examples below.

There is, thus, a need for methods of preparing alternative extracts of plants which can be used as therapeutic agents, and which eventually can provide access to new compounds.

SUMMARY OF THE INVENTION

The present invention provides a method for preparing aqueous extracts of vegetals, particularly of plants, as well as the compositions obtained by this method, some of which find application in medicine, particularly in the treatment of immune-suppressant diseases such as cancer, tuberculosis, influenza, common cold, allergies, lupus erythematosus, psoriasis and AIDS, or in the treatment of viral diseases such as hepatitis.

An aspect of the invention relates thus to a method for preparing aqueous extracts of vegetals, particularly of plants, which comprises the following steps:
 a) Decontamination of the plant
 b) Comminuting the plant.
 c) Treatment of the comminuted plant with a laser radiation.
 d) Suspension of the mixture obtained in step c) in water.
 e) Maceration of the suspension obtained in step d).
 f) Separation of the resulting liquid.

A second aspect of the invention relates to the compositions or aqueous extracts (hydrolates) obtained by the present method.

A further aspect of the invention relates to the use of the present composition as therapeutic agent in the treatment of immune suppressant diseases such as cancer, tuberculosis, influenza, common cold, allergies, lupus erythematosus, psoriasis and AIDS; or in the treatment of viral diseases such as hepatitis.

A further aspect of the invention relates to pharmaceutical compositions comprising the aqueous extracts obtained by the present method.

The method of the invention differs from those of the cited related art in the fact that the comminuted plant is treated with a laser radiation.

As demonstrated in the examples below, the treatment of the comminuted plants with the laser results in either the presence of new activities or in unexpectedly high increments of the activities of the extracts. Therefore, the extracts thus obtained have to necessarily be different from those obtained by methods which do not effect the laser treatment.

This application is associated with a co-pending U.S. patent application Ser. No. 10/432,795 entitled "Polysaccharide Compound Having Immune Stimulating Activity", identified by attorney docket no. P03,0208, and based on International Patent Application no. PCT/IB00/01946, herein incorporated by reference.

DETAILED DESCRIPTION OF THE PREFERRED EMBODIMENTS

As mentioned above, the first aspect of the invention relates to a method for preparing aqueous extracts of vegetals, particularly of plants, which comprises the steps of:
 a) Decontamination of the plant
 b) Comminuting the plant.
 c) Treatment of the comminuted plant with a laser radiation.
 d) Suspension of the mixture obtained in step c) in water.
 e) Maceration of the suspension obtained in step d).
 f) Separation of the resulting liquid.

The term "plant" defines either a unit or several units of the same species, or several units of different species, or part or parts of a plant such as stems, leaves, flowers, etc.

Step A

The decontamination is effected by washing the plant with water. The amount of water employed in this step is not determinant, and can be varied depending on the contamination state of the plant. Although higher and lower temperatures are possible, the water temperature should be between 10 and 40° C., preferably between 20 and 35° C., and most preferably 28° C. A washing tunnel can be employed to facilitate this step. Both the amount of water and the time the plant remains in the washing tunnel are not determinant, and can therefore be varied depending on the contamination state of the plant. The washing step can be carried out several times, with a drying step in between. This drying step is preferably effected by placing the plant in the sun.

Step B

Once the plant has been thoroughly decontaminated, it is comminuted by conventional methods such as a comminuting machine or even manually. Although higher and lower temperatures are possible, the temperature at which the plant is comminuted should be between 10 and 40° C.

Step C

The comminuted plant is next subjected to a treatment with laser radiation. As source of the laser radiation, a red linear laser diode with a capability of harmonic generation in wavelengths within the range of 150 to 810 nm is preferably employed. The wavelength of the laser radiation is more preferably of 200 to 400 nm and most preferably of 250 nm. The power of the laser radiation is preferably of 1 to 60 watts, more preferably of 10 to 30 watts and most preferably of 20 watts. The spot is preferably of 1 to 6 mm, more preferably of 2 to 5 mm and most preferably of 4 mm of diameter.

The comminuted plant is exposed to the laser radiation so that the whole or most of the mixture is irradiated. This is achieved either by displacing manually the laser generator through the comminuted plant, or by passing the comminuted matter on a conveyor belt through a set of several laser generators. Preferably each kilogram of the comminuted matter is treated with the laser radiation for a period of 3 to 10 minutes, more preferably for a period of 5 minutes. Although higher and lower temperatures are possible, the temperature at which the comminuted plant is treated with the laser radiation should be between 10 and 40° C.

Step D

The laser treated matter is next suspended in water. Any commercial mineral water can be employed in this step. The suspension is effected so that 50 to 300, preferably 100 to 250, grams of the laser treated matter are present per liter of water. Although higher and lower temperatures are possible, the temperature at which the comminuted plant is suspended in water should be between 10 and 40° C.

Step E

The suspension is then kept for a period of between 5 to 20 days, preferably of 7 to 15 days, at a temperature of 2 to 10° C., preferably of 4 to 8° C., so that maceration of the mixture takes place.

Step F

Finally, after the maceration step, a separation of the liquid phase from the solid phase is effected. The solids can be pressed to facilitate the separation. The separation can be achieved by decantation alone or, preferably, by decantation followed by filtration. The filtration is preferably effected under pressure. Most preferably three consecutive press-filtrations are effected with filters of 5 µm, 1 µm and 0.22 µm. Although higher and lower temperatures are possible, the temperature at which the separation is effected should be between 10 and 40° C.

The process of the invention can be applied to any kind of plants, both monocotyledomae and dicotyledonae. It can be applied to mixtures of different plants. The whole plant can be submitted to the method of the invention, although leaves and flowers are preferred.

Non-limiting examples of families of plants to which the method of the invention can be applied are: Asteraceae, Rosaceae, Crucifrae, Labiatae, Equisetaceae, Saxifraganceae, Compositae, Araliaceae and Umbeliferae. Non-limiting examples of species of plants to which the present method can be applied are: *Mentha sativa, Pimpinella anisum, Eleutherococcus senticosus, Equinacea angustifolia, Symphytum officinalis* and *quisetum arvense*. The preferred species to which the method of the invention can be applied are *Calendula officinalis, Agrimonia eupatoria, Lepidium latifolium* and *Lamium album*.

The aqueous extracts (hydrolates or compositions) obtained by the method of the invention constitute the second aspect of the invention. Thus, compositions resulting from the application of the present method to the non-limiting examples: *Mentha sativa, Pimpinella anisum, Eleutherococcus senticosus, Equinacea angustifolia, Symphytum officinalis* and *Equisetum arvense* fall within the scope of the invention. Of special interest are the aqueous extracts obtained by applying the method of the invention to *Calendula officinalis* and to the mixture of *Agrimonia eupatoria, Lepidium latifolium* and *Lamium album*, which also fall within the scope of the invention.

It has been found that some of the aqueous extracts obtained according to the method of the invention find application in medicine. This constitutes, as mentioned above, the third aspect of the invention.

The aqueous extract obtained by applying the method of the invention to *Calendula oficinalis*, and, especially, the aqueous extract obtained by applying the method of the invention to the flowers of this plant presents activity as an immune stimulator. This activity is unexpectedly extremely high, as demonstrated in the examples showed below. It is believed that the present extract acts stimulating the lymphocyte transformation activity of the lymphocytes T, B and macrophages, although this operational theory reflects just one possibility. The extract obtained by applying the method of the invention to *Calendula oficinalis* finds, thus, application in the treatment of immune-suppressant diseases. Non-limiting examples of these diseases are cancers such as hepatic carcinoma, lung cancer, kidney cancer, colon cancer, breast cancer, prostate cancer or prostatic adenocarcinoma; brain cancers such as astrocytoma and glioblastoma; cervix cancer and blade cancer; tuberculosis, influenza, common cold, allergies, lupus erythematosus psoriasis and AIDS.

Moreover, the aqueous extract obtained by applying the method of the invention to the mixture of the plants *Agrimonia eupatoria, Lepidium latifolium* and *Lamium album* and, especially, the aqueous extract obtained by applying the method of the invention to the mixture of the leaves of the plants *Agrimonia eupatoria, Lepidium latifolium* and *Lamium album* unexpectedly presents antiviral activity. More specifically, this extract is especially active against the virus of hepatitis A, B, C, D and E. This activity is extremely high as demonstrated in the examples showed below.

Furthermore, this extract also presents a high regulatory activity of the metabolism of transaminases and bilirrubine, as well as activity as stimulator of the hepatocytic regeneration. Therefore, the extract obtained by applying the method of the invention to *Agrimonia eupatoria, Lepidium latifolium* and *Lamium album* finds application in the treatment of viral diseases. Non-limiting examples of these diseases are hepatitis A, B, C, D and E. This extract can also be applied in the treatment of liver pathologies related to high levels of transaminases and bilirrubine. Non-limiting examples of such diseases are hepatitis A, B, C, D and E; hepatic cirrhosis and hepatic carcinoma.

According to the studies and experiments made by the inventor, it is believed (although this operational theory reflects just one possibility) that the laser treatment catalyses reactions between certain compounds of the plants and/or facilitates the extraction of certain compounds of the plants, so that the presence of these compounds in the extracts results in the unexpected activities referred above.

A further aspect of the invention relates to pharmaceutical compositions comprising the aqueous extracts obtained by the present method.

The aqueous extracts according to the present invention can be employed either as such or lyophilised for preparing the pharmaceutical compositions. They can be administrated either separately, as aqueous extract or lyophilised, or in the form of pharmaceutical preparations. The drug combination may be in the form of a formulation which (1) contains the extract according to the invention alone; (2) contains one or more appropriate binders, carriers and/or further auxiliary materials, and/or (3) may further contain additional therapeutically active substances.

The carrier materials, binders and/or auxiliary materials must be pharmaceutically and pharmacologically tolerable, so that they can be combined with the other components of the formulation or preparation and do not exert adverse effects on the organism treated.

The formulations include those which are suitable for oral or parentheral (including subcutaneous, intradermal, intramuscular and intravenous) administration, even though the best route of administration is dependent on the patient's status.

The formulations can be in the form of single doses. The formulations are prepared according to methods known in the field of pharmacology. The appropriate quantities of active substances suitable for administration may vary as a function of the particularly field therapy. In general, the active substance concentration in a single-dose formulation is 5% to 95% of the total formulation.

Preferred embodiments of the invention are illustrated by the examples presented below.

Example 1

Preparation of an Aqueous Extract of Flowers of *Calendula oficinalis* According to a Standard Method Comparative Example 500 g. of flowers of *Calendula oficinalis* are placed in a wash tunnel and subjected to a thorough wash with water at about 28° C. The flowers are next comminuted with a comminuting machine. The resultant 500 g of comminuted matter are next suspended in 2 liters of water at a temperature of about 20° C. The suspension is then kept for 12 days at a temperature of 4° C. Finally, the separation of the liquid and the solid phase is effected, first by decantation of the liquid (the solids are pressed to facilitate the separation), and then, by three consecutive press-filtrations with filters of 5, 1 and 0.22 μm at a temperature of about 20° C. The process yields approximately 1.7 liters of a solution (aqueous extract) of an ochre colour.

Example 2

Preparation of an Aqueous Extract of Flowers of *Calendula oficinalis* According to the Method of the Invention 500 g. of flowers of *Calendula oficinalis* are placed in a wash tunnel and subjected to a thorough wash with water at about 28° C. The flowers are next comminuted with a comminuting machine. The resultant 500 g of comminuted matter are subjected to a treatment with a red linear laser diode with a capability of harmonic generation in a wavelength of 250 nm, a power of 20 watts and a spot of 4 mm of diameter. The treatment is effected by manually displacing the laser generator through the comminuted matter during 2.5 minutes, so that the whole or most of the mixture is irradiated. The laser treated matter is next suspended in 2 liters of water at a temperature of about 20° C. The suspension is then kept for 12 days at a temperature of 4° C. Finally, the separation of the liquid and the solid phase is effected, first by decantation of the liquid (the solids are pressed to facilitate the separation), and then, by three consecutive press-filtrations with filters of 5, 1 and 0.22 μm at a temperature of about 20° C. The process yields approximately 1.7 liters of a solution (aqueous extract) of an ochre colour.

Examples 3-14

The aqueous extracts of the plants listed below were prepared according to the procedures of Examples 1 and 2. The parts of the plants which were subjected to the processes mentioned above are indicated in parenthesis. *Equisetum arvense* (stems), *Symphytum officinalis* (leaves), *Equinacea angustifolia* (leaves and flowers), *Eleutherococcus senticosus* (leaves), *Pimpinella anisum* (leaves and flowers), and *Mentha sativa* (leaves).

The aqueous extracts obtained in the Examples 1-14 were tested in order to establish their activity as immune stimulator by quantifying the lymphocyte transformation activity (LTA). Lymphocyte transformation activity means that the lymphocytes are transformed from a dormant to an active state, which is necessary to fight diseases through an immunological mechanism, or to restore the immune system, which might be weakened by different factors. These tests were performed in vitro by adding the extracts to lymphocytes isolated from mice according to the literature reference Max, W. et al., *Journal of Natural Products*, vol. 54, no. 6, pp. 1531-1542 (1991). The incorporation of thymidine, which means replication of DNA, was monitored. This incorporation is indicative both of an increase in lymphocyte number and an increase in lymphocyte activity. The results are summarised in Table 1.

TABLE 1

| Examples | Plant | Increase LTA (%) (Standard method) | Increase LTA (%) (Method including laser treatment) |
|---|---|---|---|
| 1/2 | *Calendula oficinalis* | +277 | +1204 |
| 3/4 | *Equisetum arvense* | +26 | +123 |
| 5/6 | *Symphytum officinalis* | +43 | +211 |
| 7/8 | *Echinacea angustifolia* | +98 | +270 |
| 9/10 | *Eleutherococcus senticosus* | +106 | +280 |

TABLE 1-continued

| Examples | Plant | Increase LTA (%) (Standard method) | Increase LTA (%) (Method including laser treatment) |
|---|---|---|---|
| 11/12 | *Pimpinellaanisum* | +11 | +26 |
| 13/14 | *Menthasativa* | +12 | +28 |

From the results shown in Table 1, it is clear how the aqueous extracts prepared according to the method of the invention present higher increases in the lymphocyte transformation activity values than the aqueous extracts obtained according to the standard methods, i.e., extraction without laser treatment. Furthermore, the extremely high increase in the lymphocyte transformation activity value show by the extract of *Calendula officinalis* obtained according to the method of the invention represents a very surprising result.

Example 15

Preparation of an Aqueous Extract of the Leaves of the Plants *Agrimonia eupatoria, Lepidium latifolium* and *Lamium album* According to a Standard Method Comparative Example 250 g. of leaves of *Agrimonia eupatoria*, 250 g. of leaves of *Lepidium latifolium* and 250 g. of leaves of *Lamium album*, are placed in a wash tunnel and subjected to a thorough wash with water at about 28° C. The leaves were next comminuted with a comminuting machine. The resultant 750 g of comminuted matter are next suspended in 3 liters of water at a temperature of about 20° C. The suspension is then kept for 12 days at a temperature of 4° C. Finally, the separation of the liquid and the solid phase is effected, first by decantation of the liquid (the solids are pressed to facilitate the separation), and then, by three consecutive press-filtrations with filters of 5, 1 and 0.22 μm at a temperature of about 20° C. The process yields approximately 2.7 liters of a solution (aqueous extract) of a dark green color.

Example 16

Preparation of an Aqueous Extract of the Leaves of the Plants *Agrimonia eupatoria, Lepidium latifolium* and *Lamium album* According to the Method of the Invention 250 g. of leaves of *Agrimonia eupatoria*, 250 g. of leaves of *Lepidium latifolium* and 250 g. of leaves of *Lamium album*, are placed in a wash tunnel and subjected to a thorough wash with water at about 28° C. The leaves are next comminuted with a comminuting machine. The resultant 750 g of comminuted matter are submitted to a treatment with a red linear laser diode with a capability of harmonic generation in a wavelength of 250 nm, a power of 20 watts and a spot of 4 mm of diameter. The treatment is effected by manually displacing the laser generator through the comminuted matter during 4 minutes, so that the whole or most of the mixture is irradiated. The laser treated matter is next suspended in 3 liters of water at a temperature of about 20° C. The suspension is then kept for 12 days at a temperature of 4° C. Finally, the separation of the liquid and the solid phase is effected, first by decantation of the liquid (the solids are pressed to facilitate the separation), and then, by three consecutive press-filtrations with filters of 5, 1 and 0.22 μm at a temperature of about 20° C. The process yields approximately 2.7 liters of a solution (aqueous extract) of a dark green color.

The aqueous extracts obtained in the Examples 15 and 16 were employed in clinical tests on 28 human beings suffering from different hepatic diseases and, consequently, presented high values of transaminases (GOT, GPT, GGT), bilirrubine and high viral charges. Those patients treated with the extract obtained in Example 15 presented, after three months of treatment, a slight decrease in the transaminases and no variation of the viral charges. However, those patients treated with the extract obtained in Example 16 surprisingly presented, after two months of treatment, a symptomatic recovery, normal values of transaminases and bilirrubine, as well as an important decrease of the viral charges, even in the case of hepatitis C of strain 1-B and mutated virus.

For the purposes of promoting an understanding of the principles of the invention, reference has been made to the preferred embodiments and specific language has been used to describe these embodiments. However, no limitation of the scope of the invention is intended by this specific language, and the invention should be construed to encompass all embodiments that would normally occur to one of ordinary skill in the art. Moreover, no item or component is essential to the practice of the invention unless the element is specifically described as "essential" or "critical". Numerous modifications and adaptations will be readily apparent to those skilled in this art without departing from the spirit and scope of the present invention.

The invention claimed is:

1. A method for preparing an aqueous extract of plants, comprising:
   a) decontaminating the plants, the plants being one or more of a plant part or one or more of plant parts of various plant species;
   b) comminuting the plants;
   c) treating the comminuted plants with laser radiation for a suitable time using a laser radiation device comprised of a red linear laser diode with a capability of harmonic generation of wavelengths within the range of 150 to 810 nm, a power of 1 to 60 watts and a spot of 1 to 6 mm of diameter to obtain laser-treated plant matter;
   d) suspending the laser-treated plant matter obtained in step c) in water;
   e) macerating the suspension obtained in step d); and
   f) separating the resulting liquid so as to prepare the aqueous extract.

2. The method according to claim 1, wherein the plants comprise several plant units of the same species or several plant units of different species.

3. The method according to claim 1, wherein the plants comprise a part or parts of a plant, including stems, leaves or flowers.

4. The method according to claim 1, further comprising utilizing water for decontaminating the plants.

5. The method according to claim 1, wherein the decontaminating is effected in a washing tunnel.

6. The method according to claim 1, wherein the comminuting is effected by at least one of a manual method and utilizing a comminuting machine.

7. The method according to claim 1, wherein the wavelength is within the range of 200 to 400 nm, the power of 20 watts and the spot of 4 mm diameter.

8. The method according to claim 7, wherein the wavelength is 250 nm.

9. The method according to claim 1, wherein treating of the comminuted plants comprises, for each kilogram of the comminuted matter, treating with the laser radiation for a period of 3 to 10 minutes.

10. The method according to claim 9, wherein the period is 5 minutes.

11. The method according to claim 1, wherein the suspension is effected so that 50 to 300 grams of the laser treated matter are present per liter of water.

12. The method according to claim 11, wherein the suspension is effected so that 100 to 250 grams of the laser treated matter are present per liter of water.

13. The method according to claim 1, wherein suspending the laser treated matter comprises providing the treated comminuted plants to a storage for between 5 to 20 days at a temperature of between 2 to 10° C., so that maceration takes place.

14. The method according to claim 13, wherein the storage is between 7 to 15 days, and the temperature is between 4 to 8° C.

15. The method according to claim 1, wherein the separating of the liquid phase from the solid phase comprises decanting followed by a filtering comprising three consecutive press-filtrations with filters having a pore size of approximately 5, 1 and 0.22 µm.

16. The method according to claim 1, wherein the plants comprise monocotyledonae ordicotyledonae plants.

17. The method according to claim 1, wherein the plants belong to at least one of the following families: Asteraceae, Rosaceae, Crucifrae, Labiatae, Equisetaceae, Saxifraganceae, Compositae, Araliceae and Umbeliferae.

18. The method according to claim 1, wherein the plants belong to at least one of the following species: *Mentha sativa, Pimpinella anisum, Eleutherococcus senticosus, Equinacea angustifolia, Symphytum officinalis, Equisetum arvense, Calendula officinalis, Agrimonia eupatoria, Lepidium latifolium* and *Lamium album*.

19. The method according to claim 18, wherein the plants consist of *Calendula officinalis*.

20. The method according to claim 19, wherein the plants consist of flowers of *Calendula officinalis*.

21. The method according to claim 11, wherein the plants consist of a mixture of *Agrimonia eupatoria, Lepidium latifolium* and *Lamium album*.

22. The method according to claim 21, wherein the plants consist of a mixture of the leaves of *Agrimonia eupatoria, Lepidium latifolium* and *Lamium album*.

* * * * *